United States Patent [19]

Ohtsuki et al.

[11] Patent Number: 4,912,964
[45] Date of Patent: Apr. 3, 1990

[54] SAMPLE SUPPORTING DEVICE HAVING SMALL CONTACT REGION WITH SAMPLE SUITABLE FOR VENTILATION-CHARACTERISTICS MEASURING APPARATUS

[75] Inventors: Kazuyuki Ohtsuki, Hiratsuka; Yoshiaki Kawamura, Hadano; Yasuo Katougi, Odawara, all of Japan

[73] Assignee: Japan Tobacco, Inc., Tokyo, Japan

[21] Appl. No.: 404,922

[22] Filed: Sep. 8, 1989

Related U.S. Application Data

[63] Continuation of Ser. No. 168,272, Mar. 15, 1988, abandoned.

[30] Foreign Application Priority Data

Apr. 16, 1987 [JP] Japan .................................. 62-91931

[51] Int. Cl.⁴ ............................................ G01N 15/08
[52] U.S. Cl. ........................................................ 73/38
[58] Field of Search ............ 73/38; 277/3, 27, DIG. 7

[56] References Cited

U.S. PATENT DOCUMENTS

| | | | |
|---|---|---|---|
| 4,256,314 | 3/1981 | Berglund et al. | 277/27 |
| 4,528,841 | 7/1985 | Siems | 73/38 |

FOREIGN PATENT DOCUMENTS

| | | | |
|---|---|---|---|
| 0155963 | 12/1980 | Japan | 277/27 |
| 1356012 | 6/1974 | United Kingdom | 73/38 |

Primary Examiner—Robert R. Raevis
Attorney, Agent, or Firm—Armstrong, Nikaido, Marmelstein, Kubovcik & Murray

[57] ABSTRACT

A sample supporting device includes a cylindrical body, a sample supporting member, and a holding ring member. The sample supporting member made of a rubbery material is detachably mounted on the holding ring member, which are detachably mounted inside the cylindrical body so as to define an airtight chamber. The sample supporting member is constructed of a cylindrical outer peripheral portion, a film-shaped separating wall, and a sample supporting hole. Then, a sample such as a cigarette is supported to measure ventilation-characteristics thereof by applying suction pressure to the separating wall so as to enlarge the diameter of the sample supporting hole.

9 Claims, 12 Drawing Sheets

FIG. 8
SAMPLE MEASUREMENT

SAMPLE SUPPORTING DEVICE HAVING SMALL CONTACT REGION WITH SAMPLE SUITABLE FOR VENTILATION-CHARACTERISTICS MEASURING APPARATUS

This is a continuation, of application Ser. No. 168,272 filed Mar. 15, 1988, now abandoned.

BACKGROUND OF THE INVENTION

1. Field of the Invention

The present invention generally relates to a sample supporting device adopted to a ventilation-characteristics measuring apparatus, and, more particularly, to a cigarette supporting device used for measuring the ventilation-characteristics of a cigarette, and also to a ventilation-characteristics measuring apparatus employing such a cigarette supporting device.

2. Description of the Related Art

A ventilation-characteristics measuring apparatus is to measure a flow rate of air (i.e., a ratio of an airintake amount to a dilution amount) sucked into a sample held in an airtight chamber, from the exterior of the airtight chamber, as well as a ventilation resistance of the sample, when sucking the inside air of the airtight chamber at a predetermined flow rate.

For supporting such a light-weight and soft sample as a cigarette in the ventilation-characteristics measuring apparatus, there is used a relatively thin-walled and soft member such as a tube formed by a latex dipping method. Moreover, in an automatic measuring apparatus for measuring ventilation characteristics of a sample continuously, the support for the sample is released generally by vacuum suction because this sample supporting member serves to support and release the sample and also serves as a separator in an airtight chamber (a separator for maintaining airtightness).

Figure 1:
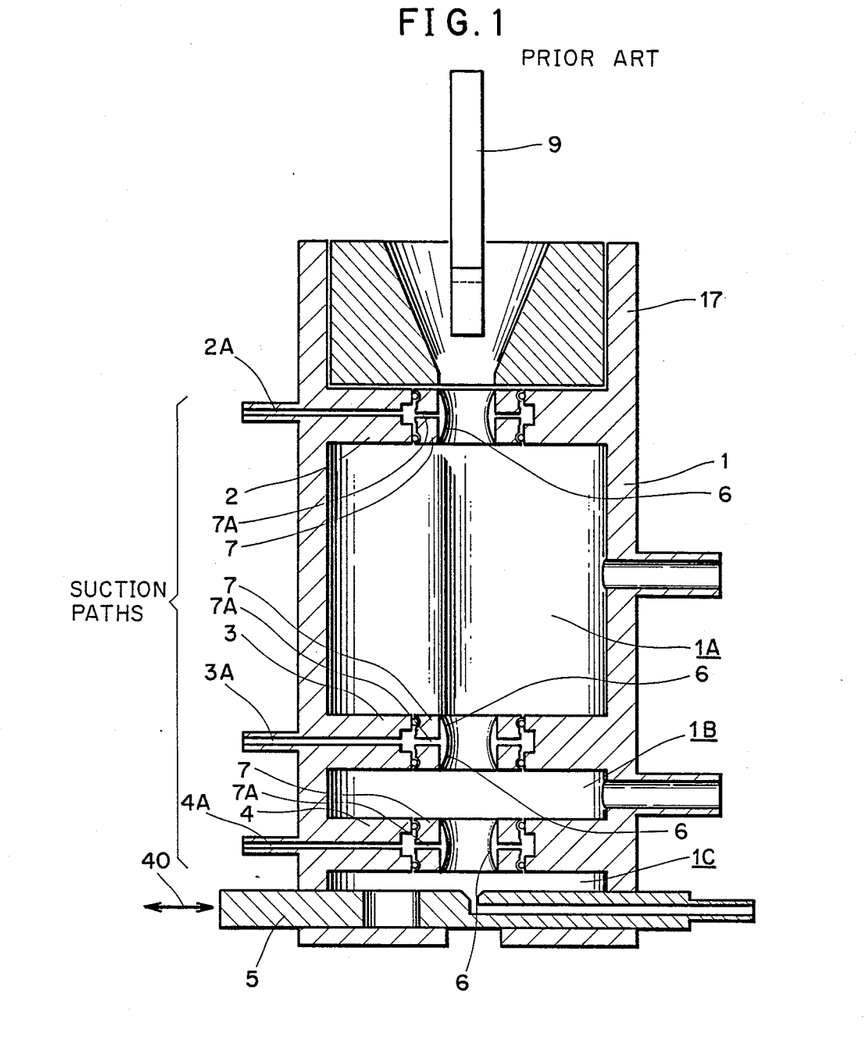
FIGS. 1, 2, 3A, and 3B are sectional views of the conventional ventilation-characteristics measuring apparatus and of the conventional sample supporting device.
Figure 2:
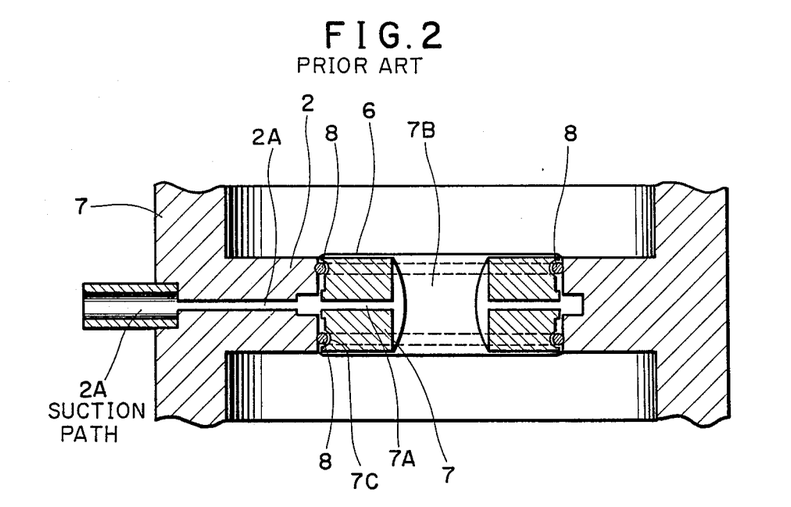

FIG. 1 shows one of conventional sample supporting devices employed in a conventional ventilation-characteristics measuring apparatus. An airtight chamber 1 is partitioned into first, second and third airtight chambers 1A, 1B and 1C in this order from above by means of flanges 2, 3 and 4. A sample stopper 5 movable in a direction of an arrow 40 is provided below the third airtight chamber 1C. In the state of FIG. 1, the stopper 5 is in operation to stop dropping of a cigarette 9. In the flanges 2, 3 and 4, suction paths 2A, 3A and 4A are formed. A holding ring 7 for mounting a sample supporting member 6 is fixed to the inside end of each of the flanges 2, 3 and 4. Each holding ring 7 is formed with a suction hole 7a communicating with the suction path 2, 3 or 4. All of the flanges—holding ring 7—sample supporting member 6 combinations are in just the same relationship. FIG. 2 shows one member of such combinations (an enlarged view).

Figure 3A:
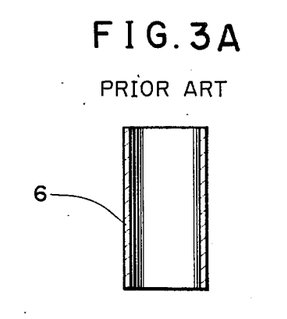
Figure 3B:
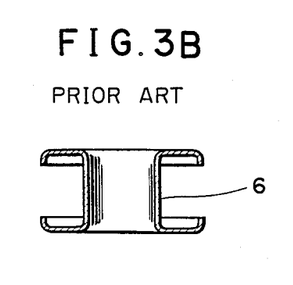

FIGS. 3A and 3B are sectional views showing the shape of the conventional sample supporting member before mounting and that after mounting respectively. The sample supporting member is integrally formed from a soft and thin-walled synthetic resin material such as a tube formed by a latex dipping method. Before mounting, it is cylindrical (FIG. 3A), while after mounting, it is of a shape with both ends thereof bent in ⊐-form with respect to a vertical axis (FIG. 3B).

As is seen from FIG. 2, the sample supporting member 6 is inserted into a central, sample supporting hole 7B of the holding ring 7 in substantially close contact with the hole. Both bent ends of the sample supporting member 6 are stretched out into close contact with the outer periphery of the holding ring 7, whereby it is mounted to the holding ring.

Further, the holding ring 7 has a groove 7C formed in the outer periphery thereof. An O-ring 8 is fitted in the groove 7C to thereby prevent the sample supporting member 6 from dropping from the holding ring 7.

In the measurement of ventilation-characteristics, the sample 9 is inserted onto the sample supporting hole 7B and its longitudinal position is defined by the sample stopper 5. At the time of the sample insertion, a negative pressure is applied to the outer periphery of the sample supporting member 6 from the exterior through the suction hole 7A. By virtue of the negative pressure, the sample supporting member 6 is brought into close contact with the inner wall of the holding ring 7, resulting in its diameter becoming a little larger than the outside diameter of the sample 9, thus permitting easy insertion of the sample into the sample supporting hole 7B. Then, upon removal of the negative pressure, the inner wall of the sample supporting member 6 expands inwards by virtue of rubbery elasticity thereof as shown in FIG. 2. That is, the diameter of the sample supporting hole 7B is reduced. Consequently, the sample 9 of a light weight is supported within the airtight chamber 9 by means of the elastic force of each sample supporting member 6. In this case, the interior of the airtight chamber 1 is partitioned into three airtight chambers 1A, 1B and 1C by three sample supporting member 6. After the end of the measurement, if a negative pressure is applied again to the outer periphery of the sample supporting member 6 through the suction paths 2A, 3A and 4A, the sample 9 will fall to the exterior of the airtight chamber 1, downwards in FIG. 1.

In the conventional sample supporting device, the support for the sample 9 by the sample supporting member 6 is effected at the inner wall surface of the sample supporting member expanded in the form of a curved surface, that is, this contact is established by "face contact". As a result, with respect to a sample having fine air-previous characteristic throughout the outer periphery thereof such as, for example, a cigarette, in the case of measuring an air intake quantity at various points of the cigarette in plural airtight chambers, it is practically impossible to obtain highly accurate measuring values, because the face contact portion is closed during the measurement. This has been a drawback.

Also in mneasuring ventilation resistance of a cigarette, there has been the problem that highly accurate measured values cannot be obtained.

The present invention has been accomplished in view of the above-mentioned drawbacks. An object of the present invention is to provide a sample supporting device for a ventilation-characteristics measuring apparatus, capable of holding a sample at a minimum contact area to permit a highly accurate measurement of ventilation characteristics of the sample.

Another object of the present invention is to provide a ventilation-characteristics measuring apparatus capable of measuring ventilation characteristics of a sample with a high accuracy.

SUMMARY OF THE INVENTION

These objects of the invention may be accomplished by providing a sample supporting device (100) comprising:

a cylindrical body (17) substantially vertically positioned, including an empty chamber communicated with a first suction path (2A:3A:4A), used for measuring ventilation-characteristics of a sample (9), said sample (9) being upwardly accepted therein, stored within said measuring empty chamber during ventilation-characteristics measurement, and released downwardly after the ventilation-characteristics measurement;

a holding ring member (107:307) having a second suction path (107:307A) communicated with said first suction path (2A:3A:4A), and detachably mounted on an inner wall of said cylindrical body (17) which defines said measuring empty chamber of the cylindrical body (17); and, a sample supporting member (106:306) made of a rubbery material, detachably mounted on said holding ring member (107:307) to be stored together with said sample (9) into said measuring empty chamber so as to define an air-tight chamber (1A:1B:1C), said sample supporting member including:

a cylindrical outer peripheral portion (106a), a flim-shaped separating wall (106B) positioned on the outer peripheral portion (106A), and projecting toward a central axis of said sample supporting member (106:306), and, a sample supporting hole (106C) formed in a tip portion of said film-shaped separating wall (106B) around the central axis of the sample supporting member (106:306), whereby while suction pressure is applied to the outer peripheral portion (106A) via said first and second suction paths of the cylindrical body (17) and holding ring member (107), a diameter of the sample supporting hole (106C) is extended, and the extended diameter is reduced to its inherent size when no suction pressure is applied thereto so as to perform insertion and release operations of the sample (9) in and from the sample holding hole (106C).

In the above construction, the support for the sample and the partition of the airtight chamber are effected by pressure contact of the thin-walled edge portion with the sample, so that the area of contact of the sample supporting member with the sample becomes extremely small, thus permitting a highly accurate measurement of ventilation characteristics.

BRIEF DESCRIPTION OF THE DRAWINGS

These and other objects and features of the present invention may be best understood by reference to the specification and the accompanying drawings, in which.

DETAILED DESCRIPTION OF THE PREFERRED EMBODIMENTS

Various embodiments of sample supporting devices according to the present invention will now be described in detail. Components same as or similar to those of the conventional example shown in FIGS. 1 to 3 will be indicated by the same reference numerals.

CONSTRUCTION OF FIRST SAMPLE SUPPORTING DEVICE

Figure 4:
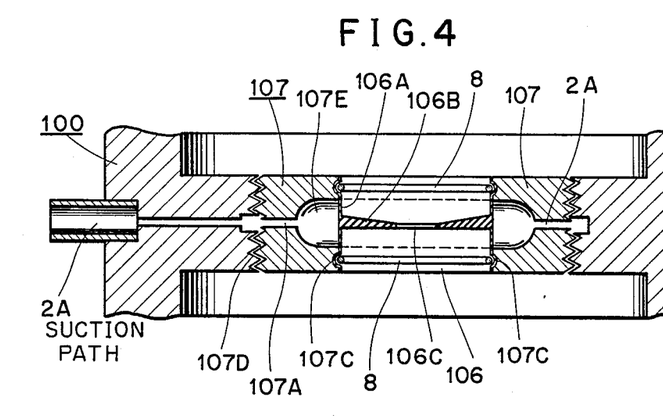
FIG. 4 is an enlarged sectional view of a first sample supporting member 106 and supporting device 100, partially illustrated, according to the present invention.
Figure 5:
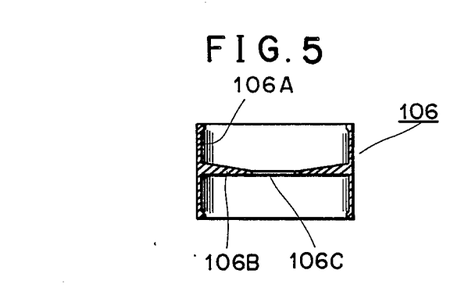
FIG. 5 is a sectional view of the first sample supporting member.
Figure 6:
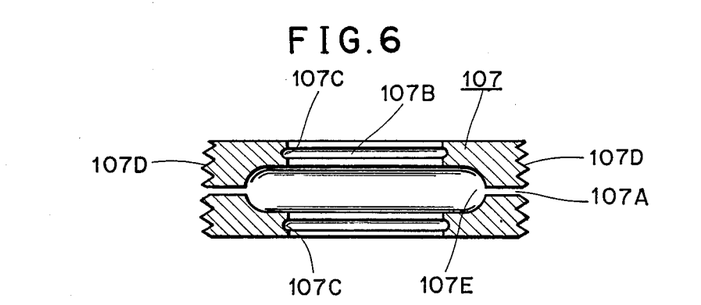
FIG. 6 is a sectional view of the first holding ring 107.

In FIGS 4 to 6, there is illustrated a sample supporting device 100 according to a first preferred embodiment of the invention.

FIG. 4 is a sectional view of a major portion of the first sample supporting device 100; FIG. 5 is a sectional view of a first sample supporting member 106; and FIG. 6 is a sectional view of a holding ring 107.

In FIGS. 4 to 6, a first sample supporting member 106 is a thin-walled, cylindrical member formed by using soft silicone and it has a chlindrical outer peripheral portion 106A, a film-shaped partition wall 106B centrally projecting inwards from the inner wall, and a sample supporting hole 106C formed in a central part of the partition wall. The outer peripheral portion 106A has a vertical length of approximately 12 mm, almost equal to the thickness of a holding ring 107. The film-shaped partition wall 106B is of a tapered section having a thick (approximately 1.5 mm) peripheral portion and a thin (approximately 0.25 mm) central portion. The diameter of the sample supporting hole 106C is set at approximately 5 mm, a little smaller than that of a sample 9.

The holding ring 107 has a threaded portion 107D on the outer peripheral side thereof, a suction chamber 107E on the inner peripheral side thereof, and two annular grooves 107C formed in upper and lower positions of the suction chamber 107E. When the threaded portion 107D comes into threaded engagement with the inner wall of the airtight chamber, the suction chamber 107E communicates with the exterior through a suction hole 107A and a suction path 2A. Further, an O-ring 8 is fitted in each of the annular grooves 107C, whereby the sample supporting member 106 is brought into close contact with the inner wall of the holding ring 107 and thereby held in place.

SAMPLE SUPPORTING OPERATION

Figure 8:
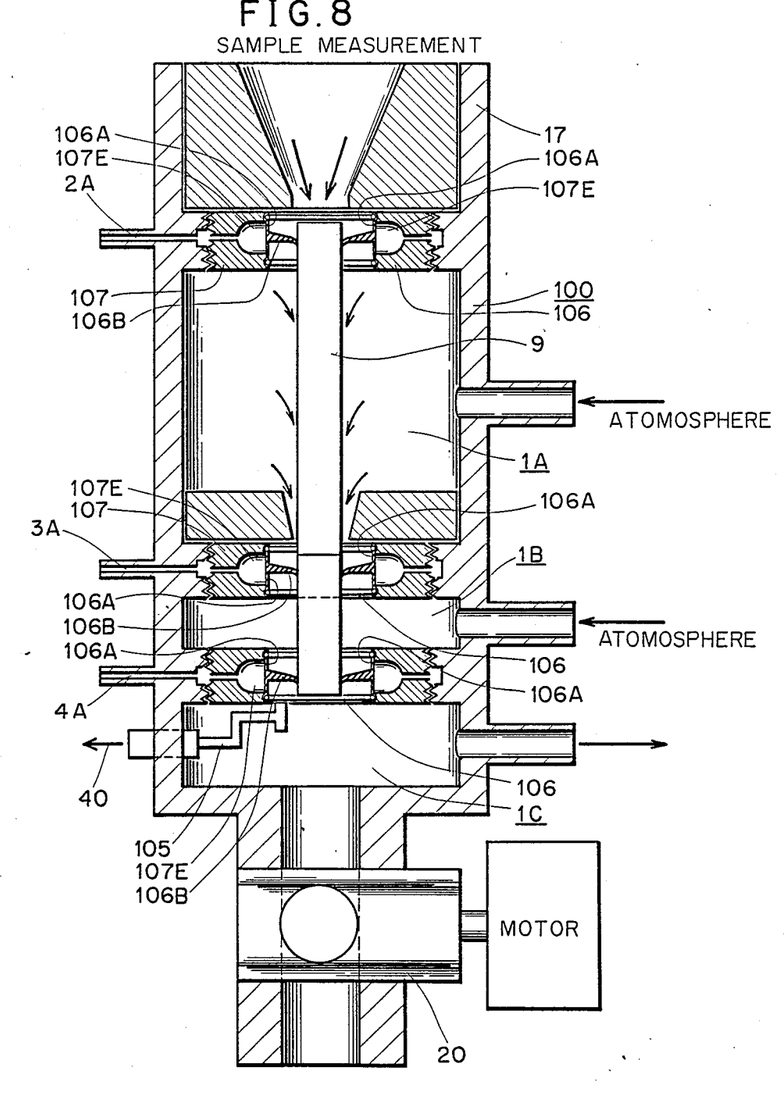
Figure 9:
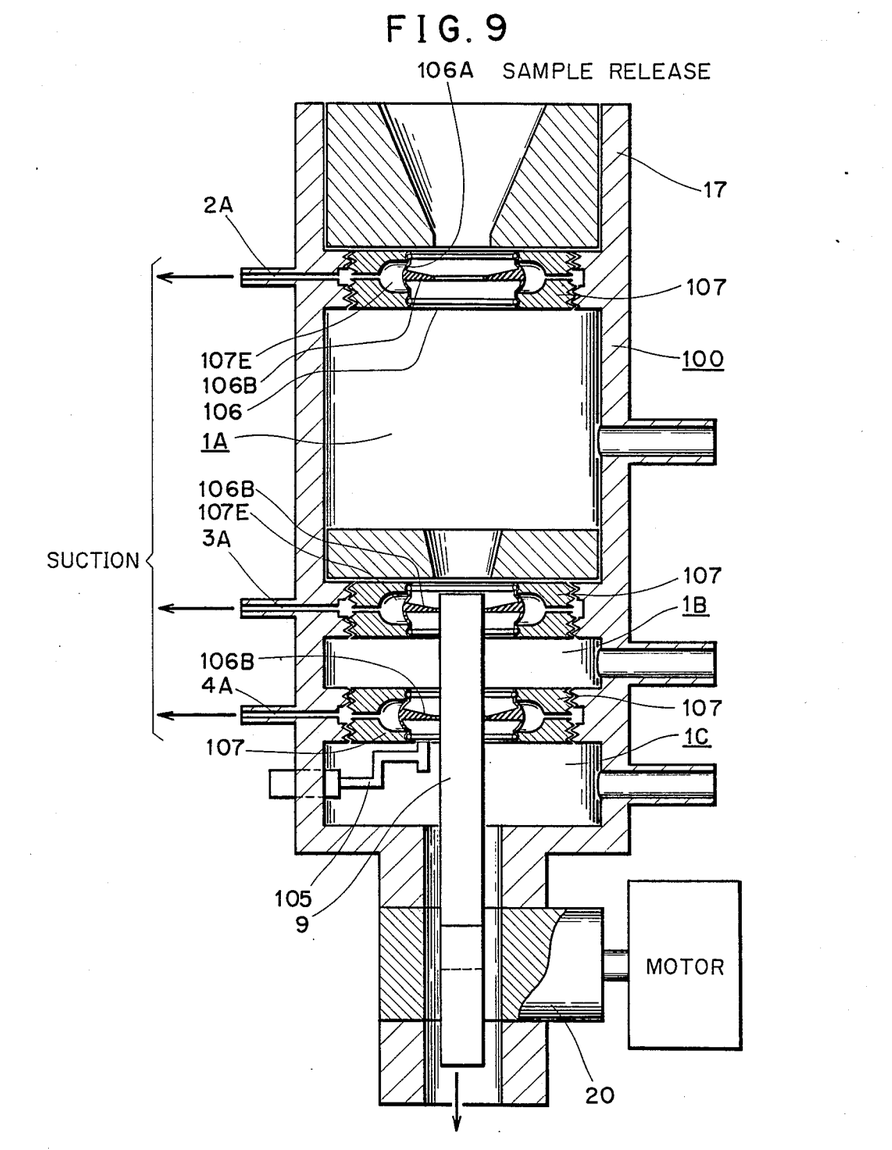

The sample supporting operation of the first sample supporting device 100 will now be described in detail with reference to FIGS. 7 to 9.

Figure 7:
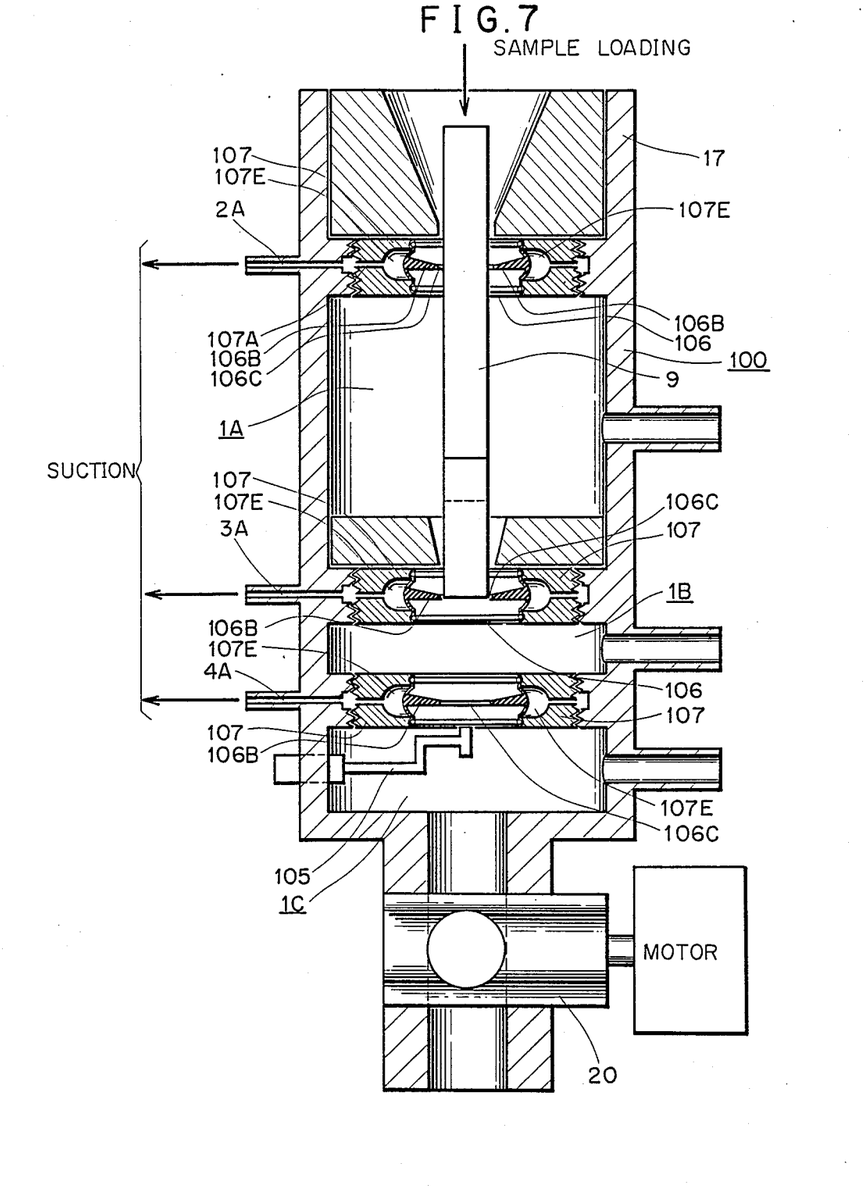
FIG. 7 to 9 schematically illustrate how the first sample supporting device 100 is operated.

First, as illustrated in FIG. 7, the first sample supporting member 106 is mounted on the first sample supporting device 100.

Next, the outer peripheral portion 106A of the sample supporting member 106 is subjected to vacuum suction from the suction chamber 107E, whereby the center of the outer peripheral portion 106A corresponding to the partition wall 106B is pulled into the suction chamber 107E, so that the diameter of the sample supporting hole 106C is expanded to approximately 12 mm as shown in FIG. 7. Under this condition, the sample 9 can be inserted from above into the airtight chambers 1A, 1B and 1C. Sample loading is now accomplished. Next, the vacuum suction is stopped and the internal pressure of the suction chamber 107E is made atmospheric. Then, a sample stopper 105 is moved in the direction of arrow 40 (see FIG. 8). As shown in FIG. 8, the outer peripheral portion 106A of the sample supporting member 106 returns to its original position and the edge portion of the partition wall 106B slightly bends downward and comes into pressure contact with the outer peripheral surface of the sample 9, whereby the sample 9 is held in place and airtight chambers 1A, 1B and 1C are hermetically sealed.

Now the preparations for sample measurement are completed. After the measurement of ventilation characteristics of the sample 9 is over, the vacuum suction is performed again to open the sample supporting hole 106C as shown in FIG. 9. As a result, the sample 9 falls downwards and is conducted to further testing, if desired. In the bottom of the sample supporting device 100, a rotary valve 20 is mounted so that the sample 9 after completion of the measurement of its ventilation-characteristics can be dropped downwards.

The sample supporting according to the preferred embodiment is effected by the inner edge of the partition wall 106B of the thin-walled sample supporting member 106. Therefore, the contact of the sample 9 with the supporting member 106 is either substantial "linear contact" or "face contact" of a small area, so that the ration of closing the outer peripheral wall (ventilation holes in the paper surface if the sample is a cigarette) of the sample 9 is small and it is possible to effect a high accuracy measurement of ventilation resistance and the ratio of air-intake amount to dilution amount. Further, good sealing for the sample 9 is ensured by the partition wall 106B.

VENTILATION-CHARACTERISTICS MEASURING APPARATUS

Figure 10:
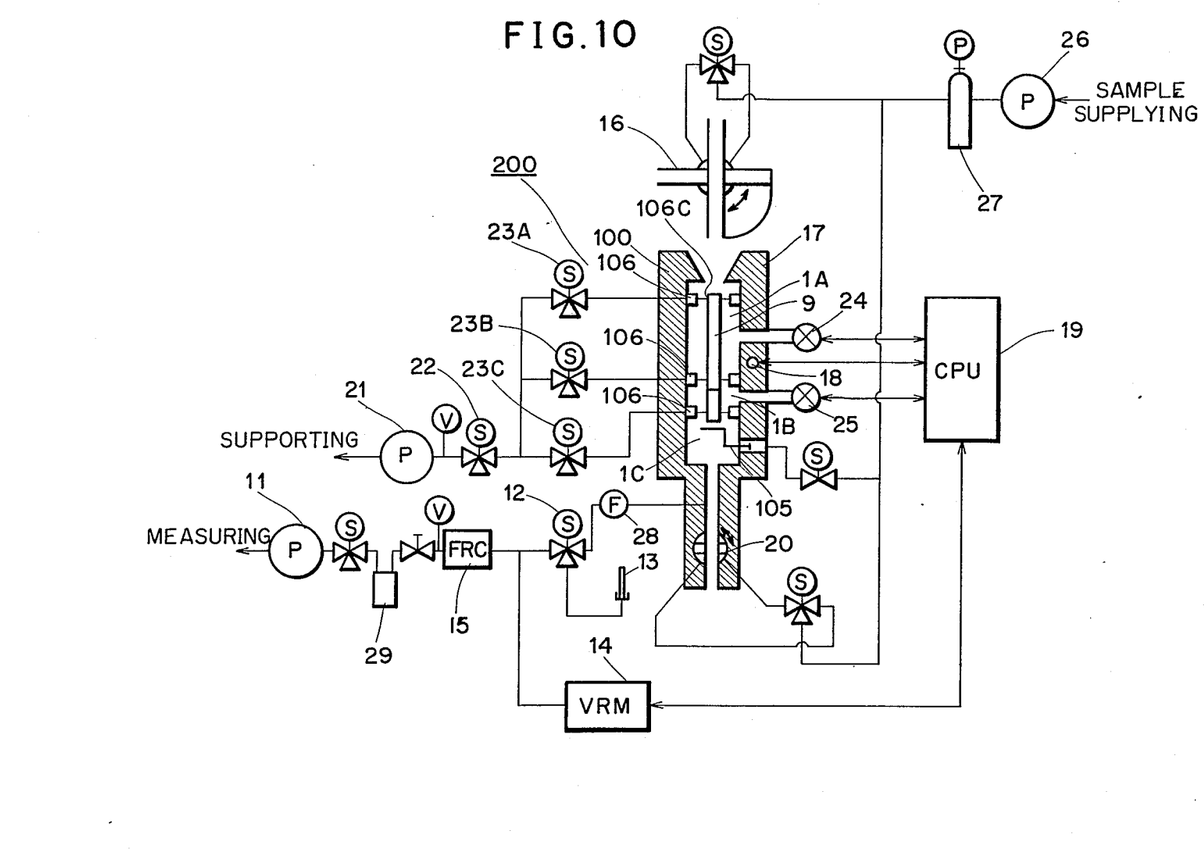
FIG. 10 is a schematic diagram of a ventilation-characteristics measuring apparatus 200 equipped with the first sample supporting device 100, according to the present invention.

The following description is now provided about a ventilation-characteristics measuring apparatus 200 suitable for the first sample supporting device 100 described above. To simplify the drawing, the first sample supporting device 100 and the sample supporting member 106 are illustrated schematically.

First, a reference flow-rate setting operation for a measuring pump 11 system is performed before the actual measurement of ventilation-characteristics.

A measurement/adjustment change-over valve 12 is set to the adjustment position and the measuring pump 11 is operated to intake air through test piece 13. At the same time, a set index for a flow-rate controller (FRC) is adjusted so that the indicated ventilation resistance of a ventilation-resistance measuring device (VRM) 14 becomes equal to the ventilation-resistance value of the test piece 13. After the end of this calibration operation, the valve 12 is set to the measurement position. The reference flow-rate setting operation is now accomplished.

The sample 9 which has processed through the previous steps (e.g., measurement of the circumference of a cigarette) is held in a horizontal state by a reversing holder 16. But if there is no sample 9 in a cylindrical body 17 of the first sample supporting device 100, a CPU 19 issues a command indicative of being ready for sample loading in accordance with a signal derived from a sample detecting sensor 18. In response to this command, the rotary valve 20 and the sample stopper 105 are closed. Further, valves 22 and 23A to 23C in a grip-seal vacuum pump system 21 are opened and the outer peripheral portion of the sample supporting member 106 is subjected to vacuum suction, so that the sample supporting hole 106C becomes larger in its diameter.

As a result, the sample 9 held in a horizontal state is dropped into the cylindrical body 17 of the first sample supporting device 100 upon 90° C. inversion of the reversing holder 16. Then, it is stopped and held by the sample stopper 105.

The sample 9 thus held in the cylindrical body 17 is detected by the sample detecting sensor 18 and a detected signal is supplied to the CPU 19. In response to the detection signal, the CPU 19 produces a command for closing the grip-seal valves 23A-23C. The valves 23A-23C are closed and the outer peripheral portion of the sample supporting member 106 (the interior of the suction chamber) becomes atmospheric in pressure, so the sample supporting hole 106C becomes smaller in diameter (i.e., becomes its original diameter) and holds the sample 9 and at the same time, seals the three airtight chambers 1A, 1B and 1C in the cylindrical body 17. Then, the sample stopper 105 is opened and measurement is started.

The measurement is performed as follows. The amount of air flowing into the airtight chamber 1A is measured by a first flow meter 24 attached to an opening of the chamber 1A; the amount of air flowing into the airtight chamber 1B is measured by a second flow meter 25 attached to an opening of the chamber 1B; and the ventilation resistance in the airtight chamber 1C is measured by the ventilation resistance measuring device 14. The resultant measuring values are input to the CPU 19 whereby the ventilation resistance of the whole of the sample 9 and also the ratios of the air-intake amount to the dilution amount at various points of the sample 9 are calculated.

After the end of the measurement, in accordance with a command supplied from the CPU 19, the rotary valve 20 opens, the grip-seal valves 23A-23C become open again, the sample supporting member 106 is drawn by suction, so the sample supporting hole 106C becomes larger in diameter, and the sample 9 is released and discharged to the next stage.

It should be noted that a series of these measuring operations are under control of the CPU 19 and various data storing memories are not shown in the drawings.

In FIG. 10, the reference numerals 26, 27, 28 and 29 denote a reversing holder driving pump, an air head, a filter and a surge tank, respectively.

Figure 11A:
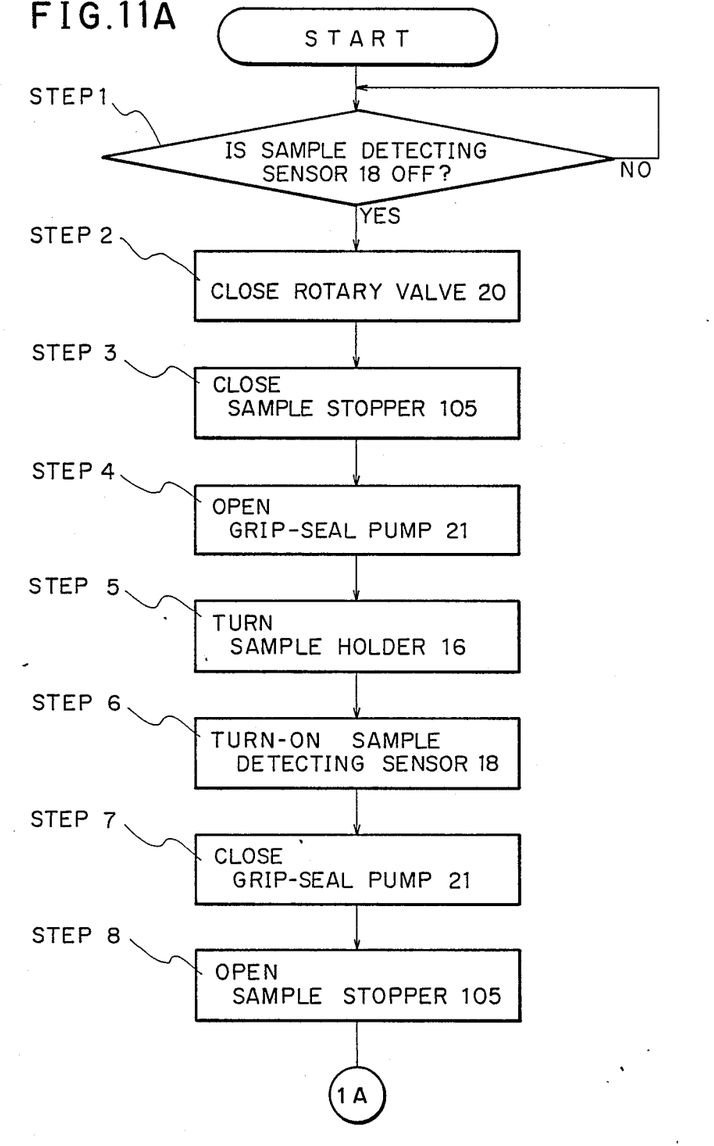
FIGS. 11A and 11B are a flowchart for explaining the ventilation-characteristics measuring operation of the measuring apparatus 200.
Figure 11B:
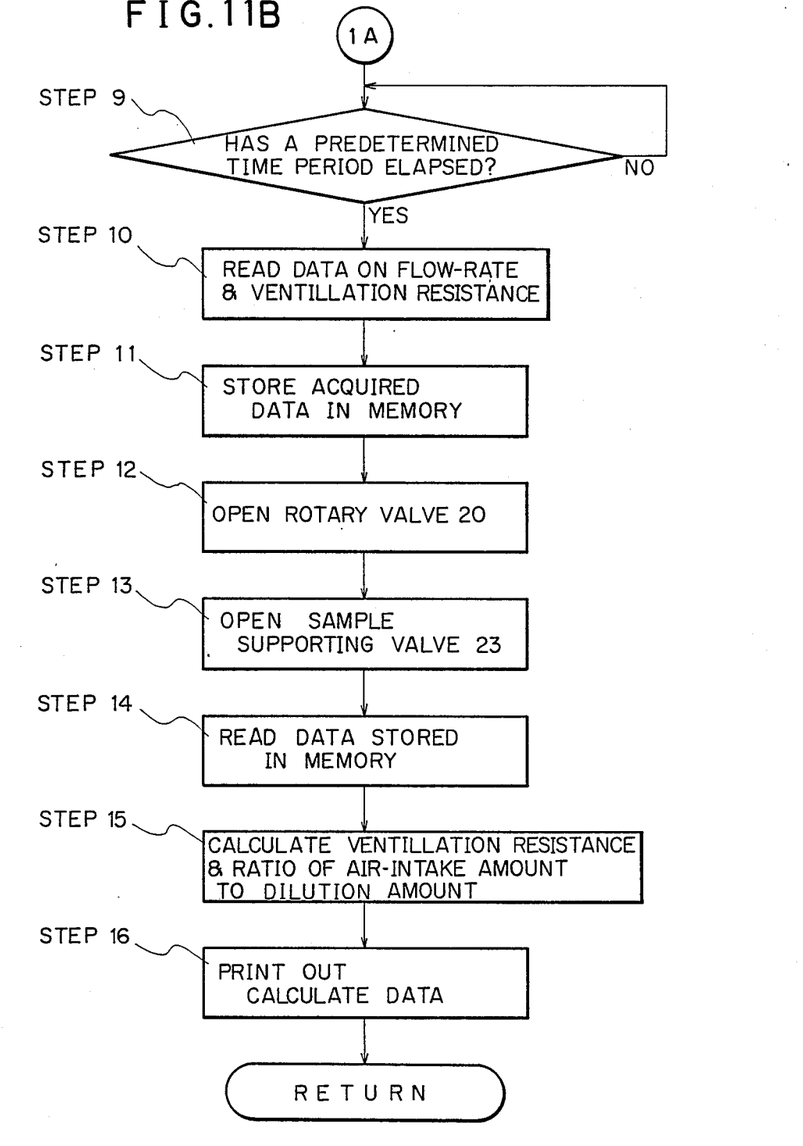

A series of the measuring operations of the ventilation-characteristics measuring apparatus 200 described above will be explained below briefly using the flow-charts of FIGS. 11A and 11B.

First, in step 1, the sample detecting sensor 18 is turned OFF and the grip-seal pump 21 is operated to load the sample 9 to be measured, from the sample holder 16 into the sample supporting device 100 positioned under the holder in FIG. 10 (step 7). Next, predetermined ventilation-characteristics are measured and after the lapse of a predetermined time (step 9), acquired data of flow rate and ventilation resistance are once stored in a memory (not shown) (step 11). Then, the sample 9 is dropped and released downwards from the sample supporting device 10 (step 13). Thereafter, the stored data are read out from the memory to the CPU 19 and a predetermined arithmetic processing is executed (step 15). Then, the result of this calculation is printed out (step 16).

MODIFICATIONS OF SAMPLE SUPPORTING MEMBER AND HOLDING RING

In practically realizing a sample supporting member having the foregoing features of the present invention, that is, a sample supporting member designed to minimize its contact area with a sample, there can be made various modifications in addition to the first sample supporting member 106 shown in FIG. 5. Such modifications will now be described in detail.

Figure 12A:
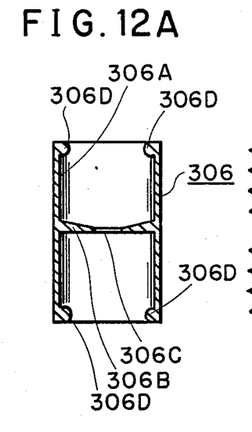
FIGS. 12A, 12B, 13A, 13B, 14A, and 14B are sectional views of second to fourth sample supporting members 306, 406, 506 and holding rings 307, 407, 507.
Figure 12B:
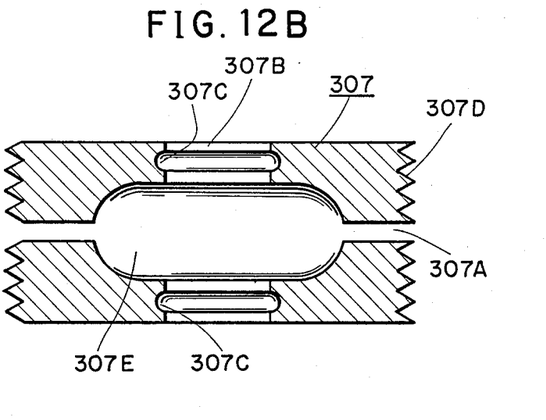

Explanation will now be made first with respect to a second sample supporting member 306 and a holding ring 307 both shown in FIGS. 12A and 12B. Edge portions of an outer periphery 306A of the second sample supporting member 306 are formed with two projections 306D, as viewed in the longitudinal direction. The projections 306D are larger than the projections formed at the edge portions of the outer periphery 106A of the first sample supporting member 106 shown in FIG. 5. On the other hand, the holding ring 307 of FIG. 12B is of the substantially same structure as the holding ring 106 of FIG. 6.

The formation of the projections 306D in this modification is characterized in that when the supporting member 306 is mounted in the holding ring 307 with O-rings 8, the O-rings are surely retained by the projections 306D of the supporting member 306.

Figure 13A:
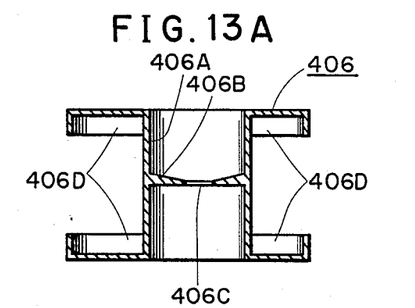
Figure 13B:
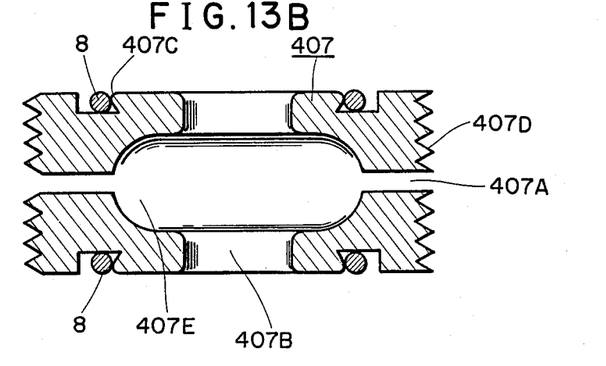

In FIGS. 13A and 13B, there are illustrated a third sample supporting member 406 and a holding ring 407, respectively. The supporting member 406 is formed in such a manner that the length (vertical direction) of an outer periphery 406A thereof is shorter than that of the outer periphery 106A of the first supporting member 106 shown in FIG. 5. The holding ring 407 has annular grooves 407C formed in positions different from the positions of the annular grooves 107C shown in FIG. 6. Further, as is apparent from FIG. 13A, the outer periphery 406A is formed with bent portion 406D.

According to this third preferred embodiment, the vertical length of the supporting member 406 and that of the holding ring 407 can be made shorter than in the first preferred embodiment. Consequently, this modification is suitable for measuring ventilation-characteristics of a tobacco having a short filter.

Figure 14A:
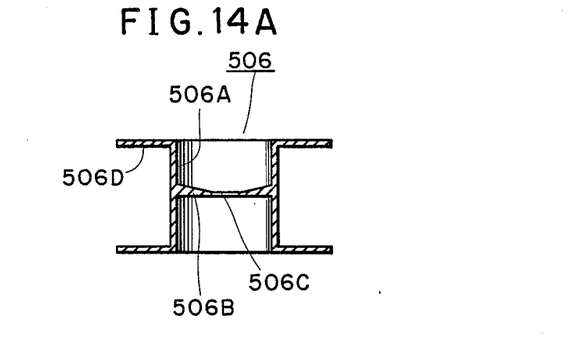
Figure 14B:
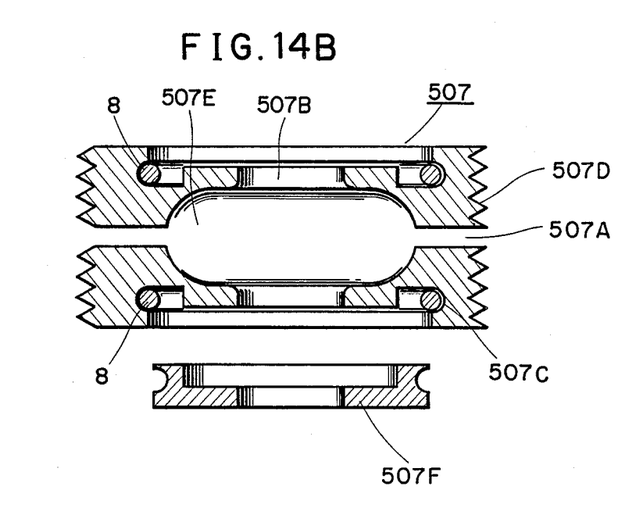

FIGS. 14A and 14B there are illustrated a fourth sample supporting member 506 and a holding ring 507, respectively. Like the third preferred embodiment described above, the length of an outer periphery 506A of the supporting member 506 is designed short and bent portions 506D are formed. Further, as shown in FIG. 14B, there are adopted a pair of seal pressers 507F for engagement with O-rings 8 received in annular grooves 507C of the holding ring 507, although the lower seal presser 507F alone is illustrated for simplification of the drawing.

The second to fourth preferred embodiments described above also have a common feature that the sample supporting members 306, 406 and 506 can be replaced easily, in addition to the other features explained above.

Figure 15:
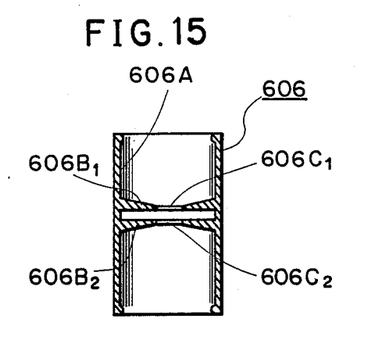
FIG. 15 to 17 are sectional views of fifth sample supporting members 606, 706, 806 according to the invention.

FIG. 15 illustrates a fifth sample supporting member 606 of a double partition wall, having tapered partition walls $606B_1$ and $606B_2$. Consequently, sample supporting holes $606C_1$ and $606C_2$ are also formed. This structure is advantageous in that the degree of close contact during the measurement of ventilation-characteristics can be enhanced.

Figure 16:
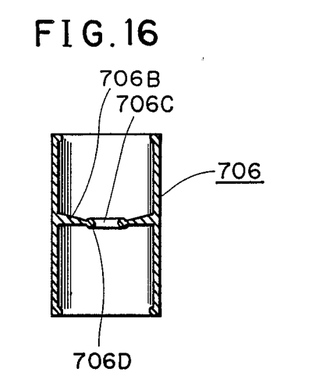

Further, FIG. 16 illustrates a sixth sample supporting member 706 having a thick-walled portion 706D formed at the tip portion of a tapered partition wall 706B. This structure is characterized in that the tip portion of the partition wall 706B is reinforced, and so effective in preventing the damage of the tip end portion in use.

Figure 17:
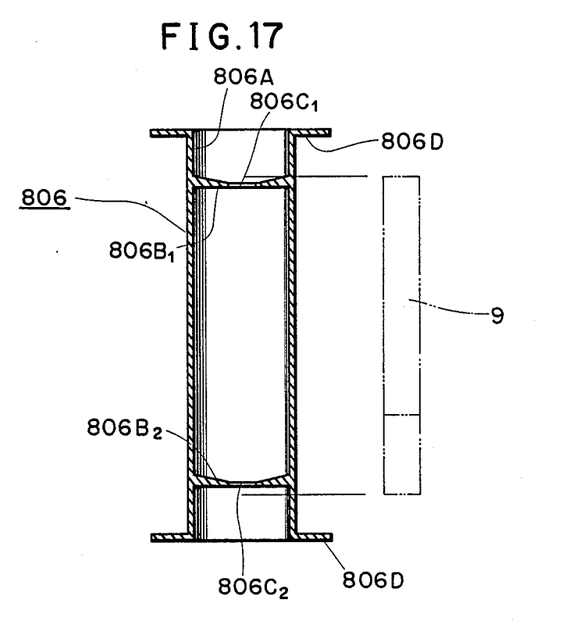

Lastly, a seventh sample supporting member 806 is illustrated in FIG. 17. The supporting member 806 is formed long in conformity with the length of the sample 9. An upper partition wall $806B_1$ is formed to seal the tip portion of the sample 9 and a lower partition wall $806B_2$ is to seal the filter of the sample. Thus, the length of the sample supporting member 806 is determined according to the vertical length of the sample 9 to be measured for ventilation-characteristics. Consequently, it is possible to obtain the supporting member 806 only for the measurement of ventilation resistance.

According to the present invention, moreover, the material of position of the sample supporting member may be selected suitably, depending upon the material or size of a sample to be measured. For example, as the material of the sample supporting member, natural rubber, chloroprene rubber, nitrile-butadiene rubber and ethylenepropylene rubber are also suitable. In the above-described preferred embodiments, a silicone rubber (hardness: Shore A 55°±5°) was used.

Further, the number of airtight chambers is not limited to three. Any appropriated member may be selected.

The features of the sample supporting member according to the present invention are summarized as follows. There is employed a sample supporting member made of an extensible material, e.g., a rubbery material, having a sample supporting hole. The diameter of the sample supporting hole changes upon application of a negative pressure to the sample supporting member. The contact area of the sample supporting wall (i.e., the tip portion of the partition wall) defining the sample supporting hole with respect to the outer peripheral portion of the sample can be minimized.

What is claimed is:

1. A sample supporting device for a ventilation measurement apparatus comprising:

a hollow cylindrical body substantially vertically positioned and having an inner wall defining an empty chamber communicated with a suction path; said empty chamber being used for measuring ventilation-characteristics of a cylindrical sample; said sample being guided into said chamber from above, positioned within said empty chamber during ventilation-characteristics measurement, and released downwardly after the ventilation-characteristics measurement;

a holding ring member mounted to said inner wall of said hollow cylindrical body coaxially therewith and having an inner wall in which a circumferential groove is formed, said groove being communicated with said suction path; and a sample supporting member positioned in said holding ring member for supporting a cylindrical sample in airtight relation within said empty chamber, said sample supporting member closing said groove and defining an annular suction chamber between said circumferential groove and said sample supporting member; wherein said sample supporting member includes:

a flexible peripheral portion having a shape of a cylinder when not sucked into said annular suction chamber and becoming protuberant when sucked into said annular suction chamber;

a filmy disk-shaped separating wall integrally formed with and coaxially provided on an inner wall of said flexible peripheral portion, said separating wall having elasticity in a radial direction thereof and flexibility in a direction in which said sample is moved; and a sample supporting hole formed in said filmy disk-shaped separating wall concentrically therewith, said sample supporting hole having a first diameter smaller than that of said sample when said flexible peripheral portion is not sucked into said annular suction chamber and a second diameter larger than that of said sample when said flexible peripheral portion is sucked into said annular suction chamber;

whereby while suction pressure is applied to said suction chamber through said suction path said diameter of said sample supporting member hole is said second diameter so that the sample is guided into said measuring chamber through the sample supporting hole and said diameter of said sample supporting member hole is said first diameter when no suction pressure is applied to said suction path so that said sample is supported with a minimum contact area in said sample supporting hole.

2. A device as claimed in claim 1, wherein said filmy disk-shaped separating wall has a tapered section.

3. A device as claimed in claim 1, wherein said filmy disk-shaped separating wall is positioned near a center portion of the flexible peripheral portion of said sample supporting member.

4. A device as claimed in claim 1, wherein said sample is a cigarette.

5. A device as claimed in claim 1, wherein said flexible peripheral portion has a pair of projections, one on each end portion thereof.

6. A device as claimed in claim 1, wherein said flexible peripheral portion has a pair of folded portions, one formed around each end portion thereof.

7. A device as claimed in claim 1, wherein said sample supporting member further includes a second filmy disk-shaped separating wall positioned parallel with said first film-shaped separating wall, and a second sample supporting hole aligned with said first sample supporting hole.

8. A device as claimed in claim 1, wherein said filmy-disk-shaped separating wall is taper-shaped in its section, a tip portion of which is reinforced with a relatively thicker wall.

9. A device as claimed in claim 1, wherein said flexible peripheral portion has a pair of folded portions, one formed around each end portion thereof, and a length to entirely enclose the sample;

a second film-shaped separating wall is positioned on the flexible peripheral portion and projecting toward a central axis of said sample supporting member in parallel with said filmy disk-shaped separating wall; and said second film-shaped separating wall further includes a second sample supporting hole aligned with said sample supporting hole.

* * * * *